(12) United States Patent
Um et al.

(10) Patent No.: US 11,306,187 B2
(45) Date of Patent: Apr. 19, 2022

(54) POLYMER-IRON OXIDE NANO-COMPLEX, USES THEREOF AND PREPARATION METHOD THEREOF

(71) Applicant: RESEARCH & BUSINESS FOUNDATION SUNGKYUNKWAN UNIVERSITY, Suwon-Si (KR)

(72) Inventors: Soong-Ho Um, Seoul (KR);
Seung-Won Shin, Seoul (KR);
Sang-Hun Chun, Incheon (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 78 days.

(21) Appl. No.: 15/901,554

(22) Filed: Feb. 21, 2018

(65) Prior Publication Data
US 2018/0243445 A1   Aug. 30, 2018

(30) Foreign Application Priority Data

Feb. 21, 2017 (KR) .................. 10-2017-0022891
Oct. 11, 2017 (KR) .................. 10-2017-0129708

(51) Int. Cl.
| | |
|---|---|
| *A61N 2/08* | (2006.01) |
| *C08J 7/043* | (2020.01) |
| *A61K 48/00* | (2006.01) |
| *C08J 7/06* | (2006.01) |
| *C09K 11/06* | (2006.01) |
| *A61N 2/00* | (2006.01) |
| *C09K 11/02* | (2006.01) |
| *C08J 3/215* | (2006.01) |
| *C12N 15/87* | (2006.01) |
| *C12N 15/88* | (2006.01) |

(52) U.S. Cl.
CPC ........... *C08J 7/043* (2020.01); *A61K 48/0041* (2013.01); *A61K 48/0083* (2013.01); *A61N 2/004* (2013.01); *C08J 3/215* (2013.01); *C08J 7/06* (2013.01); *C09K 11/025* (2013.01); *C09K 11/06* (2013.01); *C12N 15/87* (2013.01); *C12N 15/88* (2013.01); *C08J 2367/04* (2013.01); *C09K 2211/1018* (2013.01)

(58) Field of Classification Search
None
See application file for complete search history.

(56) References Cited

U.S. PATENT DOCUMENTS

2014/0248210 A1* 9/2014 Bradbury ................ A61P 35/00
424/1.29

OTHER PUBLICATIONS

Sun, Yang, et al. "Superparamagnetic PLGA-iron oxide microcapsules for dual-modality US/MR imaging and high intensity focused US breast cancer ablation." Biomaterials33.24 (2012): 5854-5864. (Year: 2012).*

(Continued)

*Primary Examiner* — Nissa M Westerberg
(74) *Attorney, Agent, or Firm* — NSIP Law

(57) ABSTRACT

The present disclosure relates to a polymer-iron oxide composite nanoparticle, a polymer-iron oxide composite nanoparticle including a silica coating layer coated on the surface of the polymer-iron oxide composite nanoparticle, a DNA-containing polymer-iron oxide composite nanostructure including DNA attached on the silica coating layer, a method of preparing the same and a method of controlling expression of a gene.

1 Claim, 20 Drawing Sheets
(14 of 20 Drawing Sheet(s) Filed in Color)

(56) References Cited

OTHER PUBLICATIONS

Malvindi, Maria Ada, et al. "Toxicity assessment of silica coated iron oxide nanoparticles and biocompatibility improvement by surface engineering." PloS one 9.1 (2014): e85835. (Year: 2014).*
Gemeinhart, Richard A., Dan Luo, and W. Mark Saltzman. "Cellular fate of a modular DNA delivery system mediated by silica nanoparticles." Biotechnology progress 21.2 (2005): 532-537. (Year: 2005).*
Wang, Lin, Wenjun Zhao, and Weihong Tan. "Bioconjugated silica nanoparticles: development and applications." Nano Research 1.2 (2008): 99-115. (Year: 2008).*
Zhu, Ningning, et al. "Tris (2, 2'-bipyridyl) cobalt (III)-doped silica nanoparticle DNA probe for the electrochemical detection of DNA hybridization." Analytica chimica acta 481.2 (2003): 181-189. (Year: 2003).*
Moura CC, Segundo MA, das Neves J, Reis S, Sarmento B. Co-association of methotrexate and SPIONs into anti-CD64 antibody-conjugated PLGA nanoparticles for theranostic application. International journal of nanomedicine. 2014;9:4911. (Year: 2014).*
Okassa, Lazare Ngaboni, et al. "Optimization of iron oxide nanoparticles encapsulation within poly (d, l-lactide-co-glycolide) sub-micron particles." European Journal of Pharmaceutics and Biopharmaceutics 67.1 (2007): 31-38. (Year: 2007).*
Kumar MN, Sameti M, Mohapatra SS, Kong X, Lockey RF, Bakowsky U, Lindenblatt G, Schmidt CH, Lehr CM. Cationic silica nanoparticles as gene carriers: synthesis, characterization and transfection efficiency in vitro and in vivo. Journal of nanoscience and nanotechnology. Sep. 1, 2004;4(7):876-81. (Year: 2004).*
Lee KY, Lee KH, Park JW, Kim DM. Flexible programming of cell-free protein synthesis using magnetic bead-immobilized plasmids. PLoS One. Mar. 28, 2012;7(3):e34429. (Year: 2012).*
Perez et al., "Preparation of Hybrid Fe3O4/Poly(lactic-co-glycolic acid) (PLGA) Particles by Emulsion and Evaporation Method. Optimization of the Experimental Parameters", Macromol. Symp., 2014, vol. 335, pp. 62-69.

* cited by examiner

POLYMER-IRON OXIDE NANO-COMPLEX, USES THEREOF AND PREPARATION METHOD THEREOF

CROSS-REFERENCE TO RELATED APPLICATIONS

This application claims priority from Korean Patent Application No. 10-2017-0022891 filed on Feb. 21, 2017 and No. 10-2017-0129708 filed on Oct. 11, 2017 with the Korean Intellectual Property Office, the disclosure of which is incorporated herein in its entirety by reference.

TECHNICAL FIELD

The present disclosure relates to a polymer-iron oxide composite nanostructure, a use thereof and a method of preparing the same.

BACKGROUND

Iron oxide nanoparticles are one of the noticeable substances in the field of biomedical treatment and diagnosis because they have the electromagnetic property, biocompatibility, and good imaging effect caused by their nano-scaled size. Such iron oxide nanoparticles are variously applicable because of the "superparamagnetism," which is a particular property of nano-sized particles. These iron oxide nanoparticles having superparamagnetism have been used in a wide range of biomedical fields such as drug delivery, photothermal therapy, separation of fine particles, and MRI imaging. However, the conventional iron oxide nanoparticles have an issue that they have weak magnetic field reactivity and superparamagnetism in a magnetic field as a single particle so that the application of iron oxide-based drug delivery system or bioimaging system has limitation.

Techniques for capturing iron oxide nanoparticles in multiple ways have been developed in order to address the limitations as described above. However, there are still limitations on the number of iron oxide nanoparticles to be captured for each technique and the magnetic field reactivity. For example, CHEN, Ou, et al. researchers in Department of Chemistry, Massachusetts Institute of Technology synthesized iron oxide nanoparticle clusters consisting of iron oxide nanoparticles using the coagulation phenomenon caused by the hydrophobic effect of the iron oxide nanoparticles. However, it was difficult to control the reactivity to the magnetic field by controlling the number or ratio of iron oxide nanoparticles captured inside although the cluster was synthesized in the regular and uniform type.

Therefore, there is a demand for nanostructures which can have more fast and accurate drug delivery and bioimaging effects and overcome the limitations of conventional iron oxide-based biomedical applications and weak reactivity to external magnetic fields (See Korean Patent Publication No. 10-2007-0106412).

Meanwhile, the gene expression includes a transcription process in which mRNA is synthesized from DNA and a translation process in which a protein is formed from the mRNA. The gene expression can be regulated by inhibiting the transcription process or translation process. Since gene expression can generally be regulated by preventing enzymes and genomes from binding to each other using a substance that binds to enzymes or genomes used in the transcription process or translation process, the desired gene expression cannot be selectively regulated, and another gene expression regulatory network can be invaded. In other words, there was an issue that a method for regulating the specific gene expression in a cell can induce an unexpected disturbance in the cell.

Therefore, in order to address the issues of the prior art, the present inventors have provided a polymer-based platform capable of including a plurality of iron oxide nanoparticles and regulating the amount of iron oxide nanoparticles in a wide range. Further, they have provided a gene expression regulator using physical shielding as a novel application of iron oxide nanoparticles prepared thereby.

More specifically, the weak magnetic field reactivity of single iron oxide nanoparticles is overcome using the polymer-based iron oxide nanostructures. Therefore, this method physically inhibits the transcription of the DNA attached to the surface of the composite using the phenomenon that the polymer-iron oxide composites cohere with each other in the magnetic field, finally thereby selectively regulating the specific gene expression without disturbing other gene expression mechanism in the cell.

However, the issue to be addressed by the present disclosure is not limited to the issues as described above, and other issues not described above can be clearly understood by those skilled in the art from the following description.

SUMMARY

The first aspect of the present disclosure may provide a polymer-iron oxide composite nanostructure including a polymer-iron oxide composite nanoparticle and a silica coating layer coated on a surface of the polymer-iron oxide composite nanoparticle.

The second aspect of the present disclosure may provide a method of preparing a polymer-iron oxide composite nanostructure, the method including: mixing a polymer and an iron oxide nanoparticle in an organic solvent, adding an aqueous solution of polyvinyl alcohol (PVA), stirring the same, and evaporating the organic solvent to obtain a polymer-iron oxide composite nanostructure; and coating the surface of the polymer-iron oxide composite nanostructure with silica.

The third aspect of the present disclosure may provide a DNA-containing polymer-iron oxide composite nanostructure including: a polymer-iron oxide composite nanoparticle; a silica coating layer coated on a surface of the polymer-iron oxide composite nanoparticle; and DNA attached on the silica coating layer.

The fourth aspect of the present disclosure may provide a method of preparing a DNA-containing polymer-iron oxide composite nanostructure, the method including: mixing a polymer and an iron oxide nanoparticle in an organic solvent, adding an aqueous solution of polyvinyl alcohol (PVA), stirring the same, and evaporating the organic solvent to obtain a polymer-iron oxide composite nanostructure; coating the surface of the polymer-iron oxide composite nanostructure with silica; substituting a surface of the silica coating with an amine group; and reacting the DNA having glutaraldehyde at the terminal thereof with the amine group to attach the DNA to the silica.

The fifth aspect of the present disclosure may provide a method of reducing expression of a gene, the method including applying a magnetic field to a DNA-containing polymer-iron oxide composite nanostructure according to the third aspect, thereby reducing the expression of the gene encoded by the DNA.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The patent or application file contains a least one drawing executed in color. Copies of this patent or patent application publication with color drawing(s) will be provided by the Office upon request and payment of the necessary fee.

DETAILED DESCRIPTION

Figure 1:
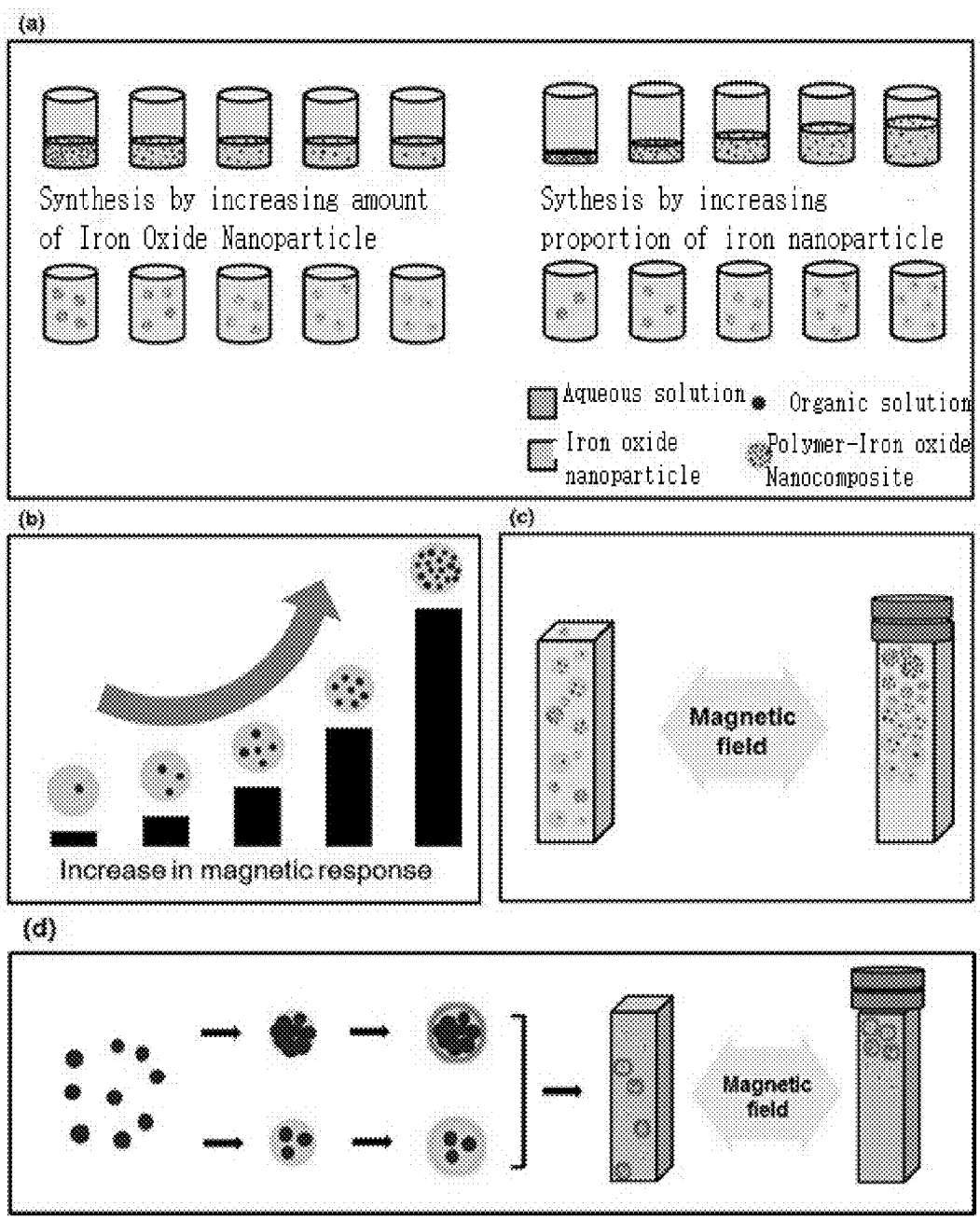
FIG. 1 is a view illustrating a method and an effect of preparing a polymer-iron oxide nanocomposite according to an embodiment of the present disclosure.

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented here.

Hereinafter, embodiments of the present disclosure will be described in detail with reference to the accompanying drawings so that the present disclosure can be easily carried out by those skilled in the art. However, the present disclosure may be embodied in various forms and is not limited to the embodiments described herein. In order to clearly describe the present disclosure in the drawings, parts not related to the description are omitted.

As used in the specification, when a portion "includes" an element, another element may be further included, rather than excluding the existence of the other element, unless otherwise described.

As used in the specification, the terms "about" and "substantially" are used to indicate that a manufacturing tolerance or a material tolerance is approximately equal to the disclosed numerical value and also to prevent disclosures, in which an accurate or absolute numerical value is presented to help the understanding of the inventive concept, from being unjustly used by an unscrupulous infringer.

As used in the specification, the term "step of" does not mean "step for."

As used in the specification, the term "combination(s) thereof" included in an expression of a Markush form means a mixture or combination of one or more elements selected from the group consisting of the elements described in the expression of the Markush form, which means including one or more selected from the group consisting of the elements.

As used in the specification, "A and/or B" means "A, B, or A and B."

Hereinafter, a polymer-iron oxide composite nanostructure, a method of preparing the same, and a method of reducing gene expression using the same are described in detail with reference to embodiments, examples and drawings. However, the present disclosure is not limited to these embodiments, examples and drawings.

The first aspect of the present disclosure may provide a polymer-iron oxide composite nanostructure including a polymer-iron oxide composite nanoparticle and a silica coating layer coated on a surface of the polymer-iron oxide composite nanoparticle.

The polymer-iron oxide composite nanostructure according to the present disclosure may be used for the treatment and diagnosis of diseases. Therefore, in an embodiment of the present disclosure, a polymer-iron oxide nanoparticle is prepared, and then the surface of the nanoparticle is coated with silica so that the iron oxide nanoparticle may be captured in multiple ways. (See Example 2) In this embodiment, poly lactic-L-glycolic acid (PLGA), a polymer, is used as a support in an embodiment of the present disclosure, but any nano-sized polymer that can be used in the living body may be used without limitation. The size of the prepared polymer-iron oxide composite may be suitably adjusted when it has a size and shape that can be injected into the body. However, but it can preferably be prepared in a spherical shape having a diameter of 200 nm to 300 nm.

Further, the polymer-iron oxide composite nanostructure of the present disclosure may further include a phosphor on a surface thereof, the phosphor may be preferably one selected from the group consisting of fluorescein, TexasRed, rhodamine, Alexa, cyanine, BODIPY or coumarin, and the phosphor may be more preferably 6-FAM, Texas 615, Alexa Fluor 488, Cy5, or Cy3. However, as long as the phosphor may be used in the living body, it is not limited thereto and can be appropriately modified and used by those skilled in the art.

Thus, the polymer-iron oxide composite nanostructure of the present disclosure has properties that it can include a large number of iron oxide nanoparticles, in addition, an amount of the iron oxide nanoparticles to be captured may be controlled in a wide range thereof, and the magnetic field reactivity and the magnetic property thereof can be precisely and easily adjusted according to the amount of the introduced iron oxide nanoparticles.

Furthermore, the polymer-iron oxide composite nanostructure of the present disclosure controls the activity of the protein treated on the surface of the polymer-iron oxide composite using 'physical shielding,' a special property of iron oxide nanoparticles, which is exhibited in the external magnetic field. Further, the polymer-iron oxide composite nanostructure has a property capable of forming the specific laminate structure and adjusting the activity of the surface-treated protein by simultaneously using the polymer-iron oxide composite nanoparticles having various magnetic properties.

The second aspect of the present disclosure may provide a method of preparing a polymer-iron oxide composite nanostructure, the method including: mixing a polymer and an iron oxide nanoparticle in an organic solvent, adding an aqueous solution of polyvinyl alcohol (PVA), stirring the same, and evaporating the organic solvent to obtain a polymer-iron oxide composite nanostructure; and coating the surface of the polymer-iron oxide composite nanostructure with silica.

More specifically, the present disclosure may provide a method of preparing a polymer-iron oxide composite nanostructure, including: mixing polymer and an iron oxide nanoparticle used as a support of the nanostructure in an organic solvent constituting an emulsion, adding an aqueous solution of polyvinyl alcohol (PVA), stirring the same, and evaporating the organic solvent to be reacted; and coating with silica based on a PVA polymer used as a surfactant in order to facilitate modification of the surface of the polymer-iron oxide composite nanostructure. The organic solvent may be chloroform, but it is not limited thereto.

In this embodiment, as long as the polymer-iron oxide composite nanostructure according to the present disclosure can be prepared by the preparation method, it may appropriately change the order and/or configuration of the steps and is not limited thereto.

The third aspect of the present disclosure may provide a DNA-containing polymer-iron oxide composite nanostructure including: a polymer-iron oxide composite nanoparticle; a silica coating layer coated on a surface of the polymer-iron oxide composite nanoparticle; and DNA attached on the silica coating layer.

The fourth aspect of the present disclosure may provide a method of preparing a DNA-containing polymer-iron oxide composite nanostructure, the method including: mixing polymer and an iron oxide nanoparticle in an organic solvent, adding an aqueous solution of polyvinyl alcohol (PVA), stirring the same, and evaporating the organic solvent to obtain a polymer-iron oxide composite nanostructure; coating the surface of the polymer-iron oxide composite nanostructure with silica; substituting a surface of the silica coating with an amine group; and reacting the DNA having glutaraldehyde at the terminal thereof with the amine group to attach the DNA to the silica.

The fifth aspect of the present disclosure may provide a method of reducing expression of a gene, the method including applying a magnetic field to a DNA-containing polymer-iron oxide composite nanostructure according to the third aspect, thereby reducing the expression of the gene encoded by the DNA.

As long as the polymer-iron oxide composite nanostructure according to the present disclosure can be prepared by the preparation method, it may appropriately change the order and/or configuration of the steps and is not limited thereto.

The polymer-iron oxide composite nanostructure according to the present disclosure may be used for the treatment and diagnosis of diseases. Therefore, in an embodiment of the present disclosure, a polymer-iron oxide nanoparticle is prepared, and then the surface of the nanoparticle is coated with silica so that the iron oxide nanoparticle may be captured in multiple ways. (See Example 2) In this embodiment, poly lactic-L-glycolic acid (PLGA), a polymer, is used as a support in an embodiment of the present disclosure, but any nano-sized polymer that can be used in the living body may be used without limitation. The size of the prepared polymer-iron oxide composite may be suitably adjusted when it has a size and shape that can be injected into the body. However, but it can preferably be prepared in a spherical shape having a diameter of 200 nm to 300 nm.

Further, the polymer-iron oxide composite nanostructure of the present disclosure may further include a phosphor on a surface thereof, the phosphor may be preferably one selected from the group consisting of fluorescein, TexasRed, rhodamine, Alexa, cyanine, BODIPY, or coumarin, and the phosphor may be more preferably 6-FAM, Texas 615, Alexa Fluor 488, Cy5, or Cy3. However, as long as the phosphor may be used in the living body, it is not limited thereto and can be appropriately modified and used by those skilled in the art.

Thus, the polymer-iron oxide composite nanostructure of the present disclosure has properties that it can include a large number of iron oxide nanoparticles, in addition, an amount of the iron oxide nanoparticles to be captured may be controlled in a wide range thereof, and the magnetic field reactivity and the magnetic property thereof can be precisely and easily adjusted according to the amount of the introduced iron oxide nanoparticles.

The third aspect of the present disclosure may provide a DNA-containing polymer-iron oxide composite nanostructure including: a polymer-iron oxide composite nanoparticle; a silica coating layer coated on a surface of the polymer-iron oxide composite nanoparticle; and DNA attached on the silica coating layer.

The expression of DNA is generally accomplished through two steps: a transcription process in which mRNA is generated from DNA and a translation process in which a protein is generated from mRNA. In these two steps, proteins called RNA polymerase and ribosome, respectively, bind to DNA and mRNA. The system provided in the present disclosure prevents RNA polymerase from binding to DNA to inhibit the transcription process, thereby reducing the production of proteins, final products.

Figure 11A:
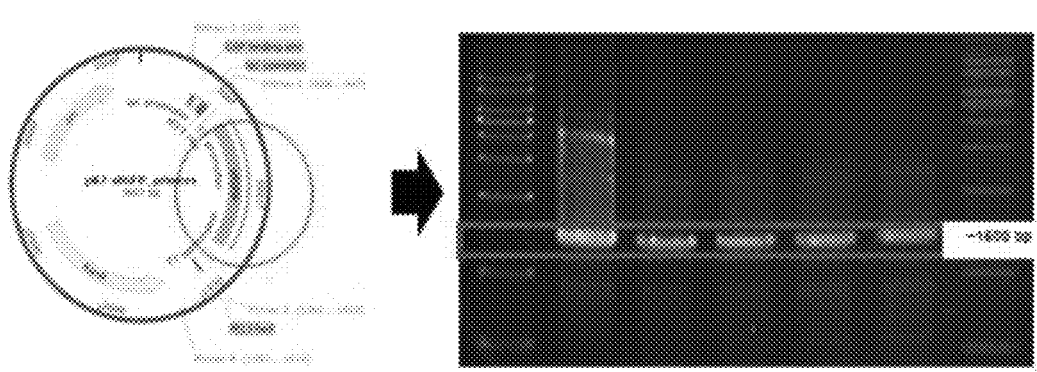
FIG. 11A illustrates the results of electrophoresis of GFP DNA prepared in an embodiment of the present disclosure.
Figure 11B:
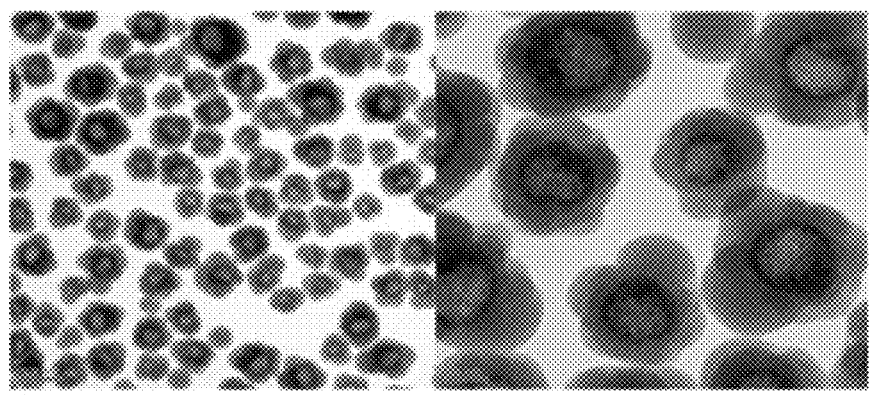
FIG. 11B illustrates the results of observation of the polymer-iron oxide nanocomposite according to an embodiment of the present disclosure by transmission electron microscope.
Figure 11C:
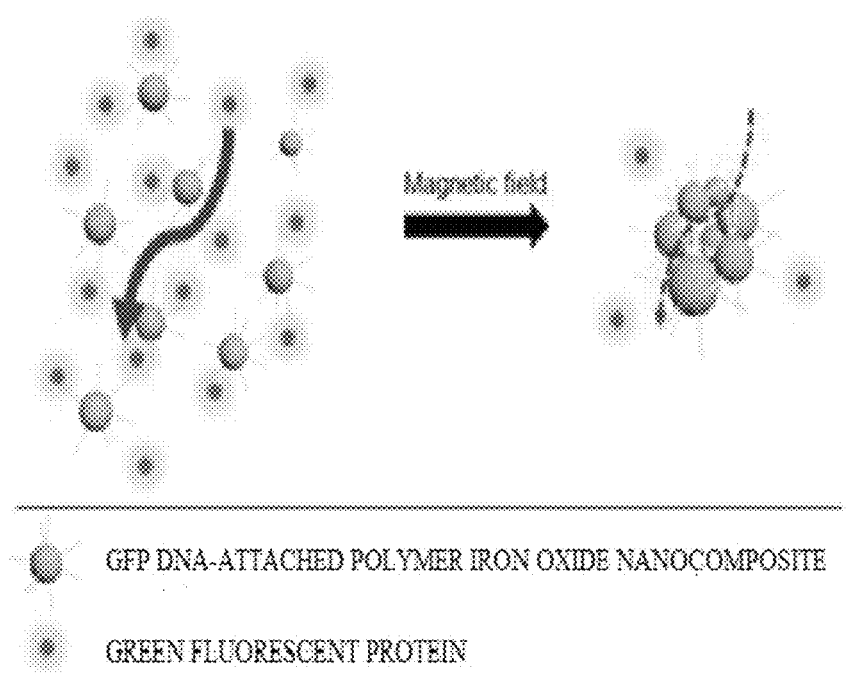
FIG. 11C illustrates a schematic diagram of a method of reducing gene expression according to an embodiment of the present disclosure.

Specifically, in order to prevent RNA polymerase from binding to DNA, DNA may be attached to a polymer-iron oxide composite nanostructure, and a magnetic field may be applied thereto so that aggregation of the nanostructure may be induced (See FIG. 11C). In this embodiment, the exposure of the DNA to the external environment including the RNA polymerase is reduced, and as a result, the production of mRNA is reduced, and therefore the preparation of proteins, final products, may be reduced.

For example, the nanostructure of the present disclosure may further include a phosphor selected from the group consisting of fluorescein, TexasRed, rhodamine, Alexa, cyanine, BODIPY, coumarin, and combinations thereof, but it may be not limited thereto.

According to an embodiment of the present disclosure, DNA may be, but is not limited to, attached to the silica coating layer by binding between glutaraldehyde at the terminal of DNA and an amine group on the silica coating layer. Any method known in the art including the present disclosure can be used without limitation as long as DNA is attached to a surface thereof by the method.

According to an embodiment of the present disclosure, the polymer may be, but is not limited to, poly lactic-L-glycolic acid (PLGA), and any nanosized polymer may be used without limitation as long as it is suitable for the living body.

According to an embodiment of the present disclosure, DNA may, but is not limited to, encode a fluorescent gene.

According to an embodiment of the present disclosure, the DNA-containing polymer-iron oxide composite nanostructure may, but not be limited to, have a diameter of about 200 nm to about 300 nm. Based on the purpose thereof, the preparing process of the nanostructure may be adjusted to adjust the diameter thereof.

The fourth aspect of the present disclosure may provide a method of preparing a DNA-containing polymer-iron oxide composite nanostructure, the method including: mixing a polymer and an iron oxide nanoparticle in an organic solvent, adding an aqueous solution of polyvinyl alcohol (PVA), stirring the same, and evaporating the organic solvent to obtain a polymer-iron oxide composite nanostructure; coating the surface of the polymer-iron oxide composite nanostructure with silica; substituting a surface of the silica coating with an amine group; and reacting the DNA having glutaraldehyde at the terminal thereof with the amine group to attach the DNA to the silica.

More specifically, the present disclosure may provide a method of preparing a polymer-iron oxide composite nanostructure, including: mixing polymer and an iron oxide nanoparticle used as a support of the nanostructure in an organic solvent constituting an emulsion, adding an aqueous solution of polyvinyl alcohol (PVA), stirring the same, and evaporating the organic solvent to be reacted; and coating with silica based on a PVA polymer used as a surfactant in order to facilitate modification of the surface of the polymer-iron oxide composite nanostructure. The organic solvent may be, but is not limited to, chloroform.

In this embodiment, as long as the polymer-iron oxide composite nanostructure according to the present disclosure can be prepared by the preparation method, it may appropriately change the order and/or configuration of the steps and is not limited thereto.

For example, the step of coating the surface of the polymer-iron oxide composite nanostructure with silica may be performed using tetraethyl orthosilicate (TEOS), but it is not limited thereto. Any technique that is typically used to form a silica layer or silica coating in the art to which the present disclosure belongs may be used without limitation.

For example, the step of substituting the silica coating surface with an amine group may be performed using (3-aminopropyl) triethoxysilane (APTES), but it is not limited thereto. Any technique that is typically used to form an amine group on a surface thereof in the art to which the present disclosure belongs may be used without limitation.

According to an embodiment of the present disclosure, the organic solvent may be, but is not limited to, chloroform. Those skilled in the art may suitably select and use one, according to the purpose thereof, from organic solvents used in the art to which the present disclosure belongs.

According to an embodiment of the present disclosure, the polymer may be, but is not limited to, poly lactic-L-glycolic acid (PLGA). Any nanosized polymer suitable for living body may be used without limitation.

The fifth aspect of the present disclosure may provide a method of reducing expression of a gene, the method including applying a magnetic field to a DNA-containing polymer-iron oxide composite nanostructure according to the third aspect, thereby reducing the expression of the gene encoded by the DNA.

According to an embodiment of the present disclosure, the expression of the gene may be reduced in a cell thereof, but it may be not limited thereto.

According to an embodiment of the present disclosure, the cell may be an animal cell, plant cell, and microbial cell, and may also be cells in vivo, but it is not limited thereto.

The DNA-containing polymer-iron oxide composite nanostructure according to the present disclosure is strongly aggregated in the magnetic field to reduce the number of DNA exposed to external through physical shielding effect so that the access of RNA polymerase is inhibited to have an effect of inhibiting gene expression of about 80% compared to the control group. This suggests novel applications of superparamagnetic materials used in various biomedical fields such as drug delivery and imaging and suggests a novel method of regulating the gene expression at the same time. Meanwhile, when a specific gene is not regulated due to an abnormality of gene expression regulatory network in the cell, the cell may develop into a cancer cell. The gene expression regulator based on the polymer-iron oxide composite provided in the present disclosure may be applied for the purpose of inhibiting or treating the generation of cancer cells by replacing the gene expression regulatory network. Hereinafter, the present disclosure is described in more detail with reference to the accompanying examples, but the following examples are only for illustrative purposes and are not intended to limit the scope of the present disclosure.

EXAMPLES

Example 1. Synthesis of Iron Oxide Nanoparticles 1-1. Synthesis of Iron Oleate
140 ml of hexane, 80 ml of ethanol and 60 ml of distilled water were placed in a 500 ml flask and stirred. Then, 10.8 g of $FeCl_3 \cdot 6H_2O$ and 36.5 g of sodium oleate were added to the flask, dissolved, and maintained at 60° C. for 4 hours. At this time, the solution was not boiled with care. After stirring for 4 hours, distilled water and ethanol were separated and removed from the lower part using a separating funnel, and the mixture was washed twice. Then, hexane was evaporated using a rotary evaporator to obtain iron oleate.

1-2. Synthesis of Iron Oxide Nanoparticles 36 g of iron oleate was added to 5.7 g of oleic acid and 200 g of 1-octadecene. The resulting mixture was rapidly stirred and dissolved. The resulting mixture was heated at 3.3° C. for 1 minute up to 320° C., was maintained at 320° C. for 30 minutes and then slowly cooled. The synthesized iron oxide nanoparticle solution was transferred to a beaker, hexane was added to the solution. Then, acetone was added to the solution until the color of the solution changes. Then, a magnet was placed on the bottom of the beaker to take away the supernatant thereof. After washing twice in the same manner as described above, a small amount of chloroform was added and dispersed in the mixture.

Example 2. Synthesis of Polymer-Iron Oxide Composite 2-1. Synthesis of Polymer-Iron Oxide Composite Nanoparticles 2-1-1. Method of Synthesizing Polymer-Iron Oxide Composite with Increasing the Ratio of Iron Oxide 20 mg of poly lactic-L-glycolic acid (PLGA) and 100 mg of iron oxide were dissolved in chloroform (0.125, 0.25, 0.5, 1, 2 and 4 ml), and then 4.5 ml of a 3% aqueous solution of polyvinyl alcohol (PVA) was added to the resulting mixture, followed by vortex for 2 minutes, and followed by dispersion for 2 minutes using an ultrasonic dispersion method. The dispersed solution was again added to 20 ml of an 1% aqueous solution of polyvinyl alcohol (PVA), the resulting mixture was stirred for 12 hours using a stirrer instead of a magnetic stirrer, thereby evaporating the chloroform. After 12 hours of stirring, the resulting mixture was washed by the centrifugation three times at 4° C. and 15,000 g for 30 minutes, and then the mixture was stored at 4° C.

2-1-2. Method of Synthesizing Polymer-Iron Oxide Composite with Increasing the Amount of Iron Oxide 20 mg of poly lactic-L-glycolic acid (PLGA) and 10, 30, 50, 70, or 100 mg of iron oxide were dissolved in 2 ml of chloroform, and then 4.5 ml of a 3% aqueous solution of polyvinyl alcohol (PVA) was added to the solution. After vortex for 2 minutes, it was dispersed for 2 minutes by an ultrasonic dispersion method. The dispersed solution was again added to 20 ml of an 1% aqueous solution of polyvinyl alcohol (PVA), the resulting mixture was stirred for 12 hours using a stirrer instead of a magnetic stirrer, thereby evaporating the chloroform. After 12 hours of stirring, the resulting mixture was washed by the centrifugation three times at 4° C. and 15,000 g for 30 minutes, and then the mixture was stored at 4° C.

2-2. Method of Treating Silica Surface of Iron Oxide-Polymer Composite Nanoparticles 4 mg of iron oxide-polymer composite was added to 20 ml of ethanol, and then 3 ml of distilled water was added to the mixture while the mixture was stirred at 700 rpm. Then, 1 ml of a 30% aqueous ammonia solution and 500 µl of tetraethyl orthosilicate (TEOS) were slowly added to the solution one by one. Then, the resulting mixture was stirred for 20 minutes and washed by centrifugation three times for 30 minutes at 20° C. and 15,000 g. After 6 hours of magnetic washing, the mixture was stored at 4° C.

Example 3. Attachment of Fluorescent Element to Polymer-Iron Oxide Composite 3-1. Substitution with Silane Source in Fluorescein Isothiocyanate (FITC)

After dissolving 19.5 mg of FITC in 50 ml of ethanol, the mixture was stirred at 800 rpm, and 11.5 µl of (3-aminopropyl) triethoxysilane (APTES) was slowly put in the mixture. Thereafter, the light was blocked, and the mixture was stirred at 42° C. for 24 hours. Then, the mixture was carefully stored so that it was not exposed to light.

40.4 ml of ethanol and 2 ml of distilled water were stirred at 800 rpm, and 250 µl of acetic acid was slowly put in the mixture. Then, 6.6 ml of the FITC solution substituted by the silane source synthesized by the method as described above was slowly added, and the mixture was stirred for 5 minutes. Thereafter, 1 ml of polymer-iron oxide solution, coated with the silica synthesized in Example 2-2 was slowly put in the mixture and the resulting mixture was stirred for 2 hours and then was washed by centrifugation three times for 30 minutes using ethanol at 20° C. and 15,000 g.

3-2. Substitution with Silane Source in Rhodamine b Isothiocyanate (RBITC)

After dissolving 19.5 mg of RBITC in 15 ml of ethanol, the mixture was stirred at 800 rpm, and 50 µl of (3-aminopropyl) triethoxysilane (APTES) was slowly put in the mixture. Thereafter, the light was blocked, and the mixture was stirred at a room temperature for 48 hours, it was carefully stored so that it was not exposed to light.

40.4 ml of ethanol and 2 ml of distilled water were stirred at 800 rpm, and 250 µl of acetic acid was slowly put in the mixture. Then, 6.6 ml of the FITC solution substituted by the silane source synthesized by the method as described above was slowly added, and the mixture was stirred for 5 minutes. Thereafter, 1 ml of polymer-iron oxide solution, coated with the silica synthesized in Example 2-2 was slowly put in the mixture and the resulting mixture was stirred for 2 hours and then was washed by centrifugation three times for 30 minutes using ethanol at 20° C. and 15,000 g.

Example 4. Confirmation of Change in Size of Polymer-Iron Oxide Composite

The size of the polymer-iron oxide composite synthesized in Example 2 and the size change after 2 weeks therefrom were confirmed through dynamic light scattering (DLS).

Figure 2A:
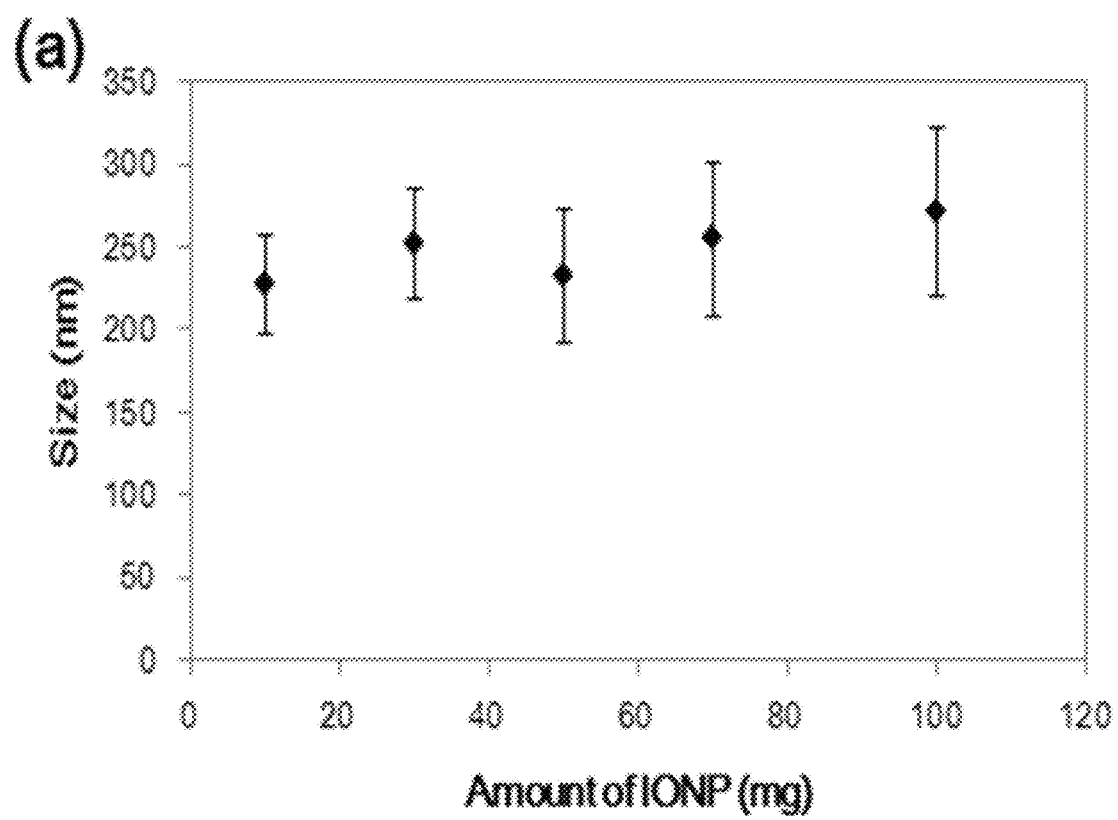
FIG. 2A is a view illustrating the size of a polymer-iron oxide composite (PLGA-iron oxide composite) measured by dynamic light scattering (DLS)
Figure 2B:
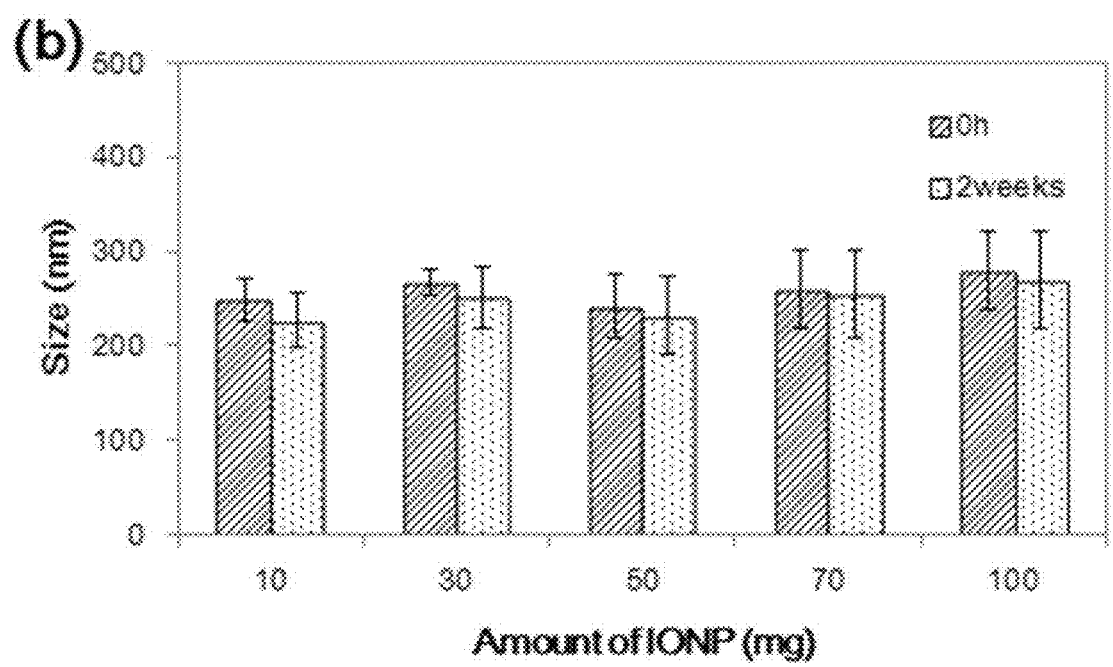
FIG. 2B is a view illustrating the size change after 2 weeks therefrom.
Figure 3:
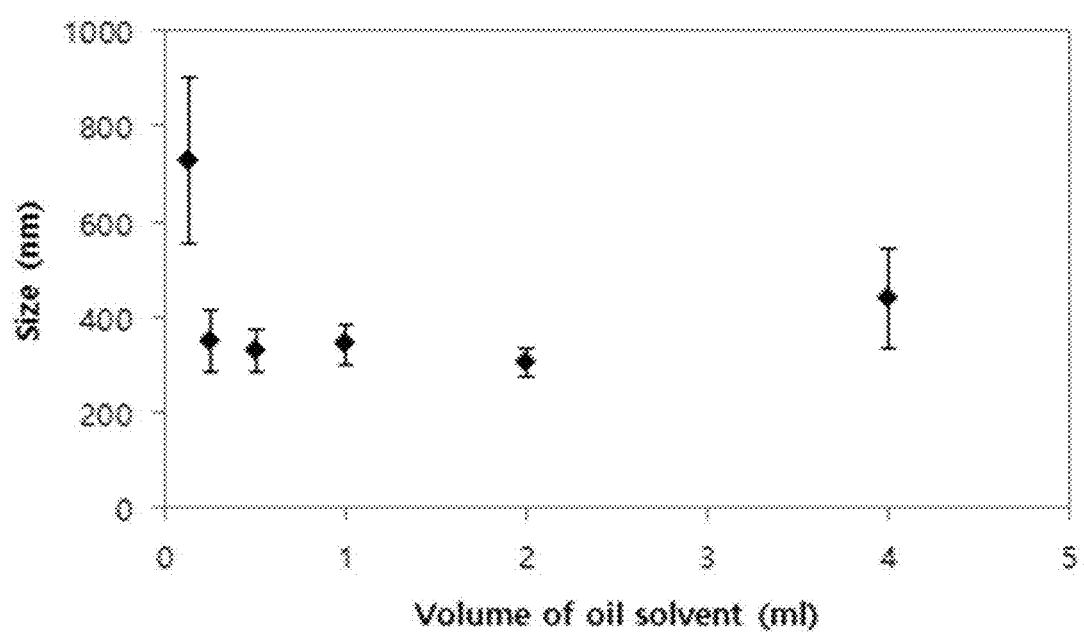
FIG. 3 is a view illustrating the result of the size of the polymer-iron oxide composite (PLGA-iron oxide composite) synthesized with different ratios of iron oxide nanoparticles, which is measured by dynamic light scattering (DLS)
Figure 4:
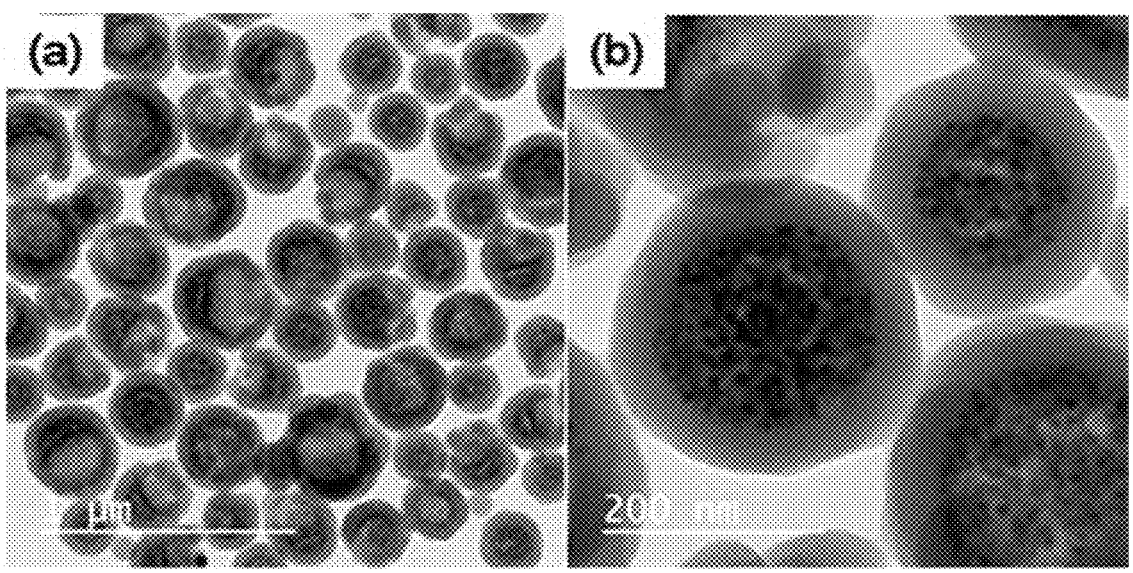
FIG. 4 includes views illustrating a silica-coated polymer-iron oxide composite (PLGA-iron oxide composite) according to an embodiment of the present disclosure, which is measured through a transmission electron microscope (TEM)

As a result, in the case of synthesizing the composite by increasing the amount of iron oxide, although the polymer-iron oxide composite (PLGA-iron oxide composite) was synthesized by increasing the amount of iron oxide to 10 times as illustrated in FIG. 2, it was confirmed that the entire size of the composite was constant. Further, it was confirmed that the size of the composite obtained even after 2 weeks remained stable without change.

Figure 6:
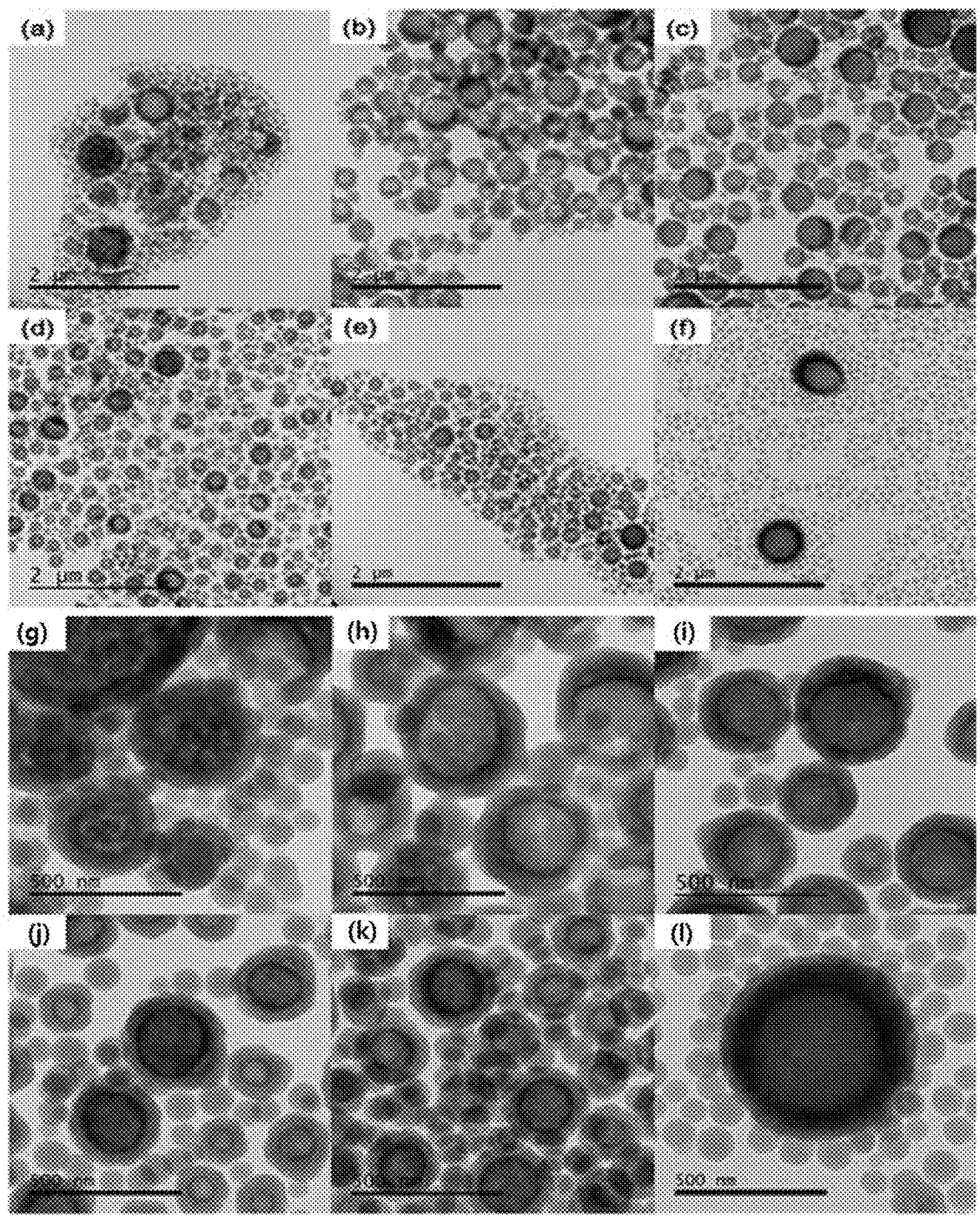
FIG. 6 includes views illustrating polymer-iron oxide composites of which the silica is coated on the surface, synthesized by increasing the proportion of iron oxide nanoparticles, which are measured through a transmission electron microscope (TEM) at various magnifications.

Meanwhile, it was confirmed that in the case of synthesizing the composite by increasing the ratio of iron oxide, as illustrated in FIG. 6, when the amount of chloroform used as the solvent is changed over a certain range, the size of the composite was significantly changed due to the property of the emulsion solvent evaporation method.

Further, the silica-coated polymer-iron oxide composite (PLGA-iron oxide composite) was examined by transmission electron microscopy (TEM). As a result, it was confirmed that all of the polymer-iron oxide composite (PLGA-iron oxide composite) was uniformly coated with silica as illustrated in FIG. 5.

Example 5. Confirmation of Change in Size of Iron Oxide in Polymer-Iron Oxide Composite The amount of iron oxide in the polymer-iron oxide composite synthesized in Example 2 and the change in the size of the composite were confirmed through transmission electron microscopy (TEM).

Figure 5:
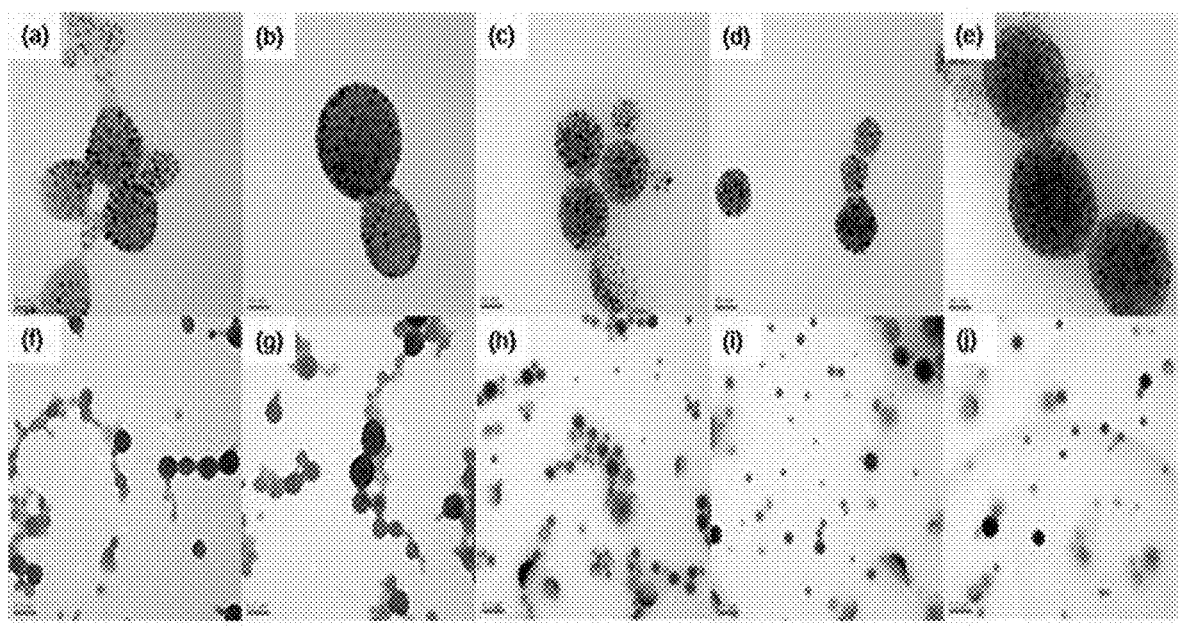
FIG. 5 includes views illustrating different silica-coated polymer-iron oxide composites (PLGA-iron oxide composites) in which the amount of iron oxide inside is adjusted differently, which are measured by a transmission electron microscope (TEM)

As a result, in the case of synthesizing the composite by increasing the amount of the iron oxide, the polymer-iron oxide composite (PLGA-iron oxide composite) synthesized using iron oxide nanoparticles of 10, 30, 50, 70, and 100 mg from the left as illustrated in FIG. 5. was observed. It was confirmed that as the amount of iron oxide increased, the amount of iron oxide captured in the composite increased, but the size of the composite as a whole was constant.

On the other hand, in the case of synthesizing the composite by increasing the ratio of iron oxide, as illustrated in FIG. 6, the ratio of iron oxide nanoparticles in the emulsion was increased in order of (a), (b), (c), (d), (e), and (f) due to the property of the emulsion solvent evaporation method.

Example 6. Confirmation of Reactivity of Polymer-Iron Oxide Composite to External Magnetic Field 500 µl of the polymer-iron oxide composite (PLGA-iron oxide composite) synthesized according to the method as described above was put in a 4.5-ml cuvette, 4 ml of water was added thereto, and the mixture was thoroughly mixed. The cap of the cuvette was closed with care to avoid air bubbles and the change in absorbance with time was measured at a wavelength of 500 nm using a spectrometer. After waiting for the absorbance of the solution to remain constant for initial 10 minutes, a magnet was placed on the top of the cuvette including the polymer-iron oxide composite (PLGA-iron oxide composite) to apply a magnetic field. Then, the change in absorbance was observed for 2 hours and 50 minutes.

Figure 7:
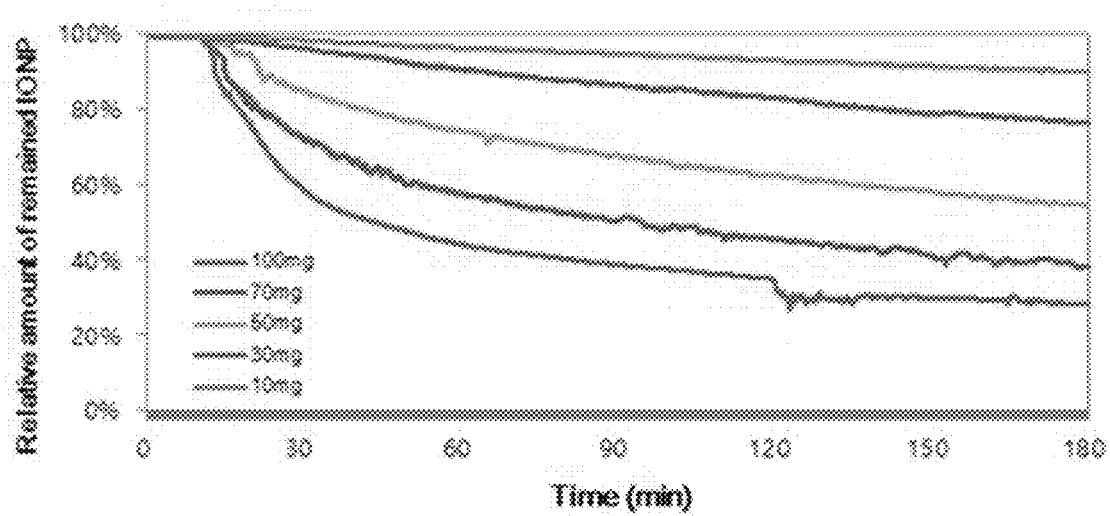
FIG. 7 is a view illustrating the reactivity of different polymer-iron oxide composites (PLGA-iron oxide composites) with different amounts of iron oxide (10 mg to 100 mg) to external magnetic fields.

As a result, in the case of synthesizing the composite by increasing the amount of iron oxide, as illustrated in FIG. 7, when the amount of iron oxide captured in the polymer-iron oxide composite (PLGA-iron oxide composite) increased as the inside iron oxide was controlled in different amounts (10 mg to 100 mg), it was confirmed that the reactivity to the magnetic field increased as the amount of iron oxide captured increased.

Figure 8:
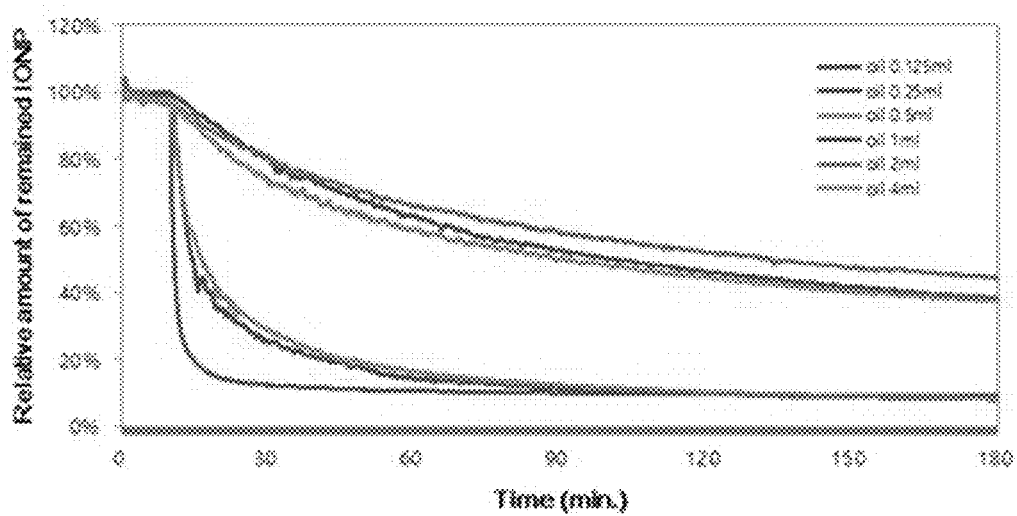
FIG. 8 is a view illustrating the reactivity of different polymer-iron oxide composites (PLGA-iron oxide composites) with different iron oxide nanoparticle ratios to external magnetic fields.

On the other hand, in the case of synthesizing the composite by increasing the ratio of iron oxide, as illustrated in FIG. 8, it was confirmed that the reactivity to the magnetic field increased as the ratio of iron oxide in the polymer-iron oxide composite (PLGA-iron oxide composite) increased. It was found that it was more remarkable difference than when the only amount of iron oxide increased simply.

In this example, the resultant value was expressed as a relative value with respect to the initial number of particles by measuring the number of remaining particles without reacting with the magnet over time.

Example 7. Confirmation of Change in Fluorescence Intensity by External Magnetic Field Using Polymer-Iron Oxide Composite Attached with Fluorescence Factor 250 µl of each of the two fluorescence factor-attached polymer-iron oxide composites (PLGA-iron oxide composite) having magnetic field reactivities different from each other, synthesized in Example 3 was added a 4.5-ml cuvette, 4 ml of distilled water was added thereto, and the mixture was thoroughly mixed. The cap of the cuvette was closed with care to avoid air bubbles. The change in fluorescence intensity with time was measured at 520 nm of the fluorescence wavelength of FITC and 570 nm of the fluorescence wavelength of RBITC at one time. After waiting for the absorbance of the solution to remain constant for initial 10 minutes, a magnet was placed on the top of the cuvette including the polymer-iron oxide composite (PLGA-iron oxide composite) to apply a magnetic field thereto. Then, the change in absorbance was observed for 2 hours and 50 minutes.

Figure 9:
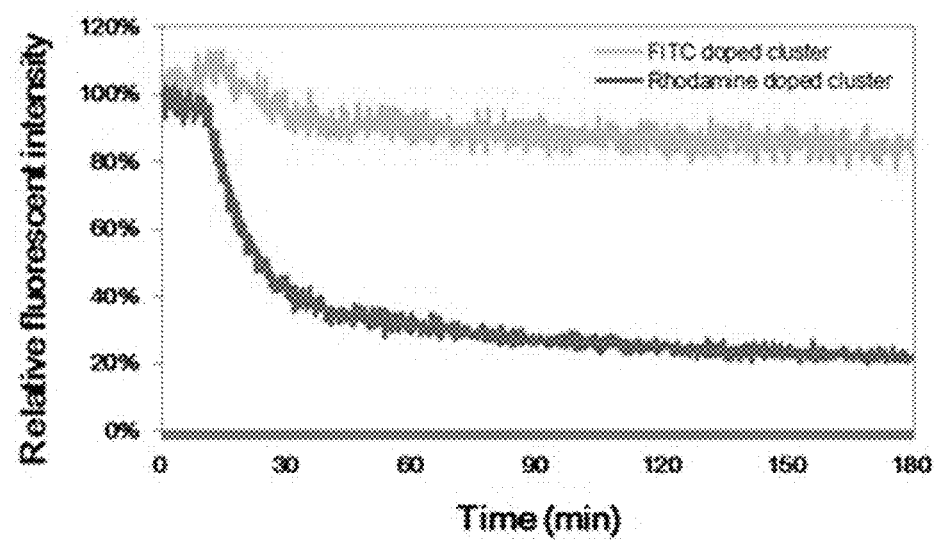
FIG. 9 is a view illustrating changes in fluorescence intensity measured when an external magnetic field is applied after attaching FITC and RBITC, fluorescent elements, to polymer-iron oxide composite (PLGA-iron oxide composite) having two different magnetic field reactivities.

As a result, as illustrated in FIG. 9, it was confirmed that the fluorescence intensity of RBITC attached to the polymer-iron oxide composite (PLGA-iron oxide composite) having stronger magnetic field reactivity was rapidly decreased than that of FITC. These results show that when polymer-iron oxide composites (PLGA-iron oxide composite) synthesized with different ratios of iron oxide are used, the rate of attraction of the attached fluorescent factors caused by the magnet will be changed. This suggests that it may be used to form a unique laminated structure.

Example 8. Formation and Confirmation of Laminated Structure Using a Fluorescent Factor-Attached Polymer-Iron Oxide Composite Therefore, on the basis of the results of Example 7, 100 µl of each of the two polymer-iron oxide composites (PLGA-iron oxide composite) having magnetic field reactivities different from each other, synthesized in Example 3, and 300 µl of 15% SDS PAGE gel solution were mixed, and the mixture was put in the tip of a micropipette whose end was closed. Then, an external magnetic field was applied thereto, and after 20 minutes, the temperature was raised to solidify the SDS PAGE gel solution. Then, the tip was cut, and the laminated structure formed in the gel was confirmed by a fluorescence microscope.

Figure 10:
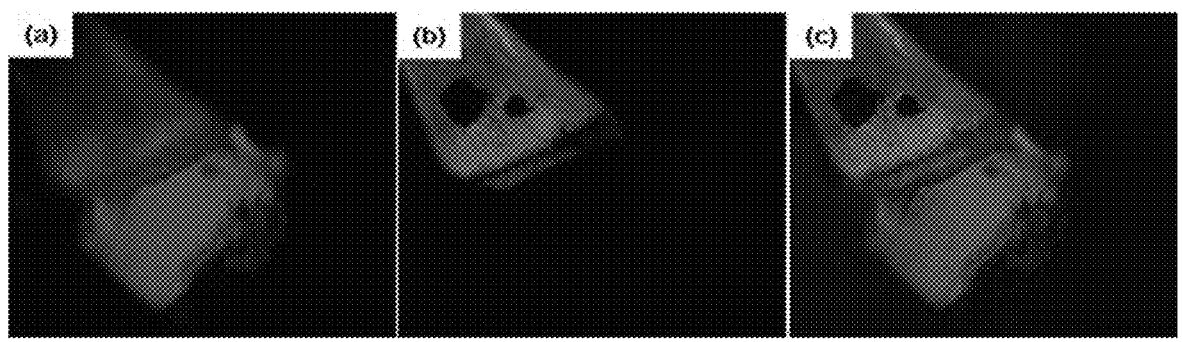
FIG. 10 includes views illustrating a laminate structure formed when an external magnetic field is applied after attaching FITC and RBITC, fluorescent elements, to polymer-iron oxide composite (PLGA-iron oxide composite) having two different magnetic field reactivities, which is measured by the fluorescence microscopy.

As a result, as illustrated in FIG. 10, it was confirmed RBITC attached to the polymer-iron oxide composite (PLGA-iron oxide composite) having a significant magnetic field reactivity (FIG. 10A) and FITC attached to the polymer-iron oxide composite (PLGA-iron oxide composite) having a small magnetic field reactivity (FIG. 10B).

Example 9. Preparation of DNA-Containing Polymer-Iron Oxide Composite 9-1. Preparation of DNA-Containing Polymer-Iron Oxide Composite 9-1-1. Polymer-Iron Oxide Composite After iron oleate was synthesized in the same manner as in Example 1-1, iron oxide nanoparticles were synthesized by the method of Example 1-2. Then, 100 mg of iron oxide synthesized in Example 1-2 was dissolved in 0.5 ml of chloroform. Thereafter, a polymer-iron oxide composite was prepared in the same manner as in Example 2-1-1.

9-1-2. Silica-Coated Polymer-Iron Oxide Composite

Thereafter, as the same manner as in Example 2-2, 5 ml (40 mg) of iron oxide-polymer composite was added to 20 ml of ethanol, and 3 ml of distilled water was added thereto while stirring at 800 rpm. Then, 1 ml of a 30% aqueous ammonia solution and 500 µl of tetraethyl orthosilicate (TEOS) were slowly added thereto in order. Thereafter, the mixture was stirred for 20 minutes and washed by centrifugation three times for 15 minutes at 20° C. and 15,000 g. After 12 hours of magnetic washing, the resulting mixture was stored at 4° C. A transmission electron microscope image of the silica-coated iron oxide-polymer composite is illustrated in FIG. 11B.

9-1-3. Treatment with Amine Group on Surface of Silica-Coated Iron Oxide-Polymer Composite 2 ml of distilled water and 0.25 ml of acetic acid were added to 45 ml of ethanol. Then, 2 ml of (3-aminopropyl) triethoxysilane (APTES) and 3 ml (25 mg) of silica-coated iron oxide-polymer composite were slowly added thereto, and the mixture was stirred at 800 rpm for 4 hours. The mixture was washed by centrifugation twice at 20° C. and 15,000 g for 15 minutes with ethanol and water, respectively. The resulting mixture was finally dispersed and stored in water.

9-1-4. Attachment of GFP DNA on Surface of Polymer-Iron Oxide Composite

Amino group-substituted primers were used to cut and amplify the site involved in GFP expression from the plasmid by polymerase chain reaction (PCR). The structure of the plasmid used and electrophoresis results of the amplified 1600 bp-sized GFP DNA are illustrated in FIG. 11A. In this example, the obtained GFP DNA has an amine group at the terminal thereof. After quantification of GFP DNA, the result was stirred with 8% glutaraldehyde at 1000 times or more in number ratio at room temperature for 24 hours, and GFP DNA substituted with glutaraldehyde was obtained through filtering. After re-quantification, 1.67 pmol of GFP DNA and 1.5 mg of amine group-treated iron oxide-polymer composite were stirred in a total volume of 0.3 ml of an aqueous solution for 24 hours at room temperature. It was washed by centrifugation three times for 10 minutes at 20° C. and 10,000 g with distilled water, then dispersed in distilled water, and stored at 4° C.

Figure 12A:
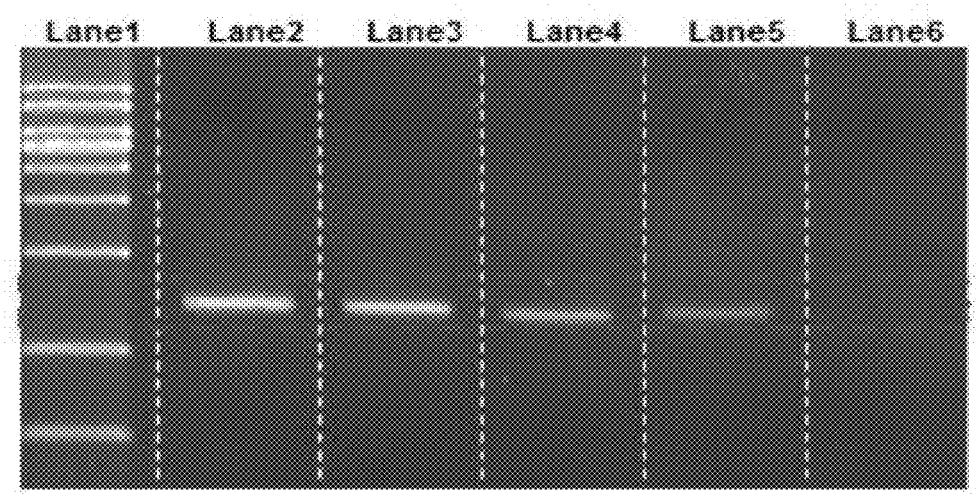
FIG. 12A illustrates the electrophoresis results obtained after attaching GFP DNA to the surface of the polymer-iron oxide composite according to an embodiment of the present disclosure.
Figure 12B:
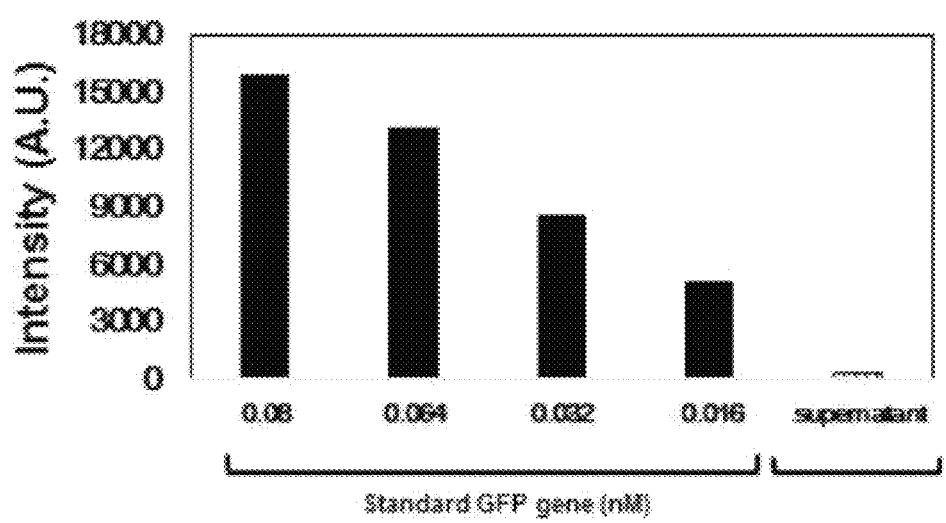
FIG. 12B is a graph illustrating results digitized therefrom.

9-1-5. Confirmation of GFP DNA Attachment on Surface of Polymer-Iron Oxide Composite According to the method described in Example 9-1-4, GFP DNA was attached to a polymer-iron oxide composite. Following the first centrifugation, 0.1 ml of the supernatant was extracted and the amount of unreacted GFP DNA was confirmed by electrophoresis. The electrophoresis was carried out at 100 V for 40 minutes on TAE buffer using 1% agarose gel. Thereafter, for 15 minutes, the resultant was stained with Ethidium bromide and was confirmed by irradiating ultraviolet rays. The result of electrophoresis using the agarose gel is illustrated in FIG. 12A. The reference DNA concentration was found in Lane 2-5, and the unreacted DNA extracted from the supernatant was found in Lane 6. FIG. 12B is a graph obtained by digitizing an electrophoresis result using an image-J program.

Example 10. Confirmation of Regular Expression of GFP DNA Attached to Surface of Polymer-Iron Oxide Composite 12 µl (0.1 pmol GFP DNA) of GFP DNA-attached polymer-iron oxide composite prepared by the method described in Example 9 was placed in a total volume of 45 µl of the DNA expression kit and incubated at 30° C. for 8 hours. The fluorescence value of the generated GFP was measured using a spectroscopic analyzer.

Example 11. Confirmation of Inhibition of Expression of GFP DNA Attached to Surface of Polymer-Iron Oxide Composite in a Magnetic Field 12 µl (0.1 pmol GFP DNA) of GFP DNA-attached polymer-iron oxide composite prepared by the method described in Example 9 was placed in a total volume of 45 µl of the DNA expression kit and incubated in an incubator having 30° C. for 8 hours. In this example, the control group was cultured without any manipulation. In the experimental group, a neodymium magnet was placed on the bottom of the tube. After 8 hours, the control group and experimental group were centrifuged at 10,000 g for 10 minutes at 4° C. 10 µl of the supernatant was extracted and diluted in 10 times, and fluorescence values of each GFP were measured and compared using a spectroscopic analyzer. The comparison result is illustrated in FIG. 13.

Figure 13:
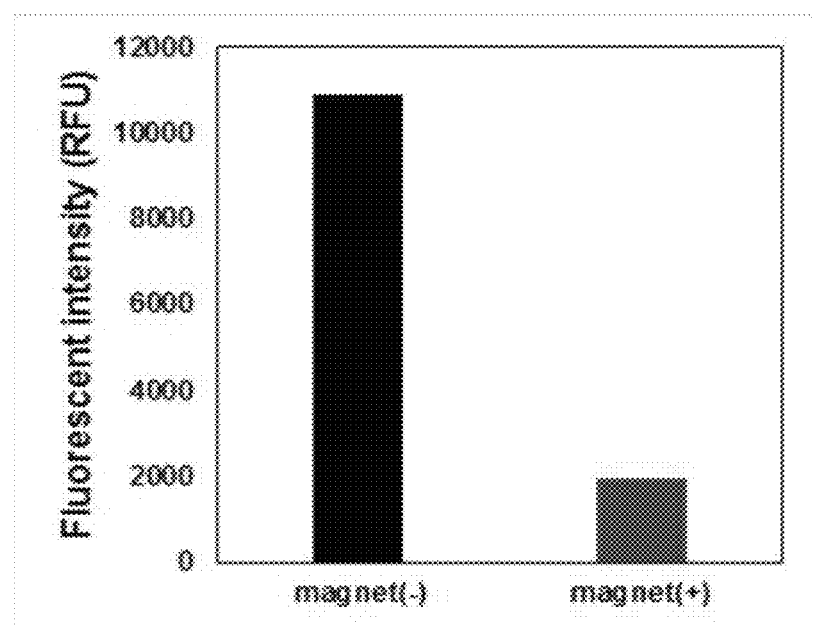
FIG. 13 is a view illustrating the results of the DNA expression regulation, according to physical shielding, of DNA-containing polymer-iron oxide composite nanostructure prepared according to an embodiment of the present disclosure.

As illustrated in FIG. 13, in the experimental group (magnetic (+)), the neodymium magnet was placed on the bottom thereof to inhibit the protein expression, and the effect of inhibiting protein expression by about 80% was confirmed.

Example 12. Comparison of Changes in the Amount of GFP DNA Expression by Culture Time 12 µl (0.1 pmol GFP DNA) of GFP DNA-attached polymer-iron oxide composite prepared by the method described in Example 9 was placed in a total volume of 45 µl of the DNA expression kit and incubated in an incubator having 30° C. A neodymium magnet was placed underneath the experimental group in order to compare the expression level of fluorescent proteins. Fluorescence values of the expressed GFP were measured every 20 minutes through a spectroscopic analyzer after the start of culture. This example was conducted three times in the same manner, and the average value thereof was measured. This example was carried out after Example 8 was performed. The difference in the amount of the fluorescent protein finally expressed was confirmed in FIG. 13. It could be confirmed how the difference occurred over time.

Figure 11D:
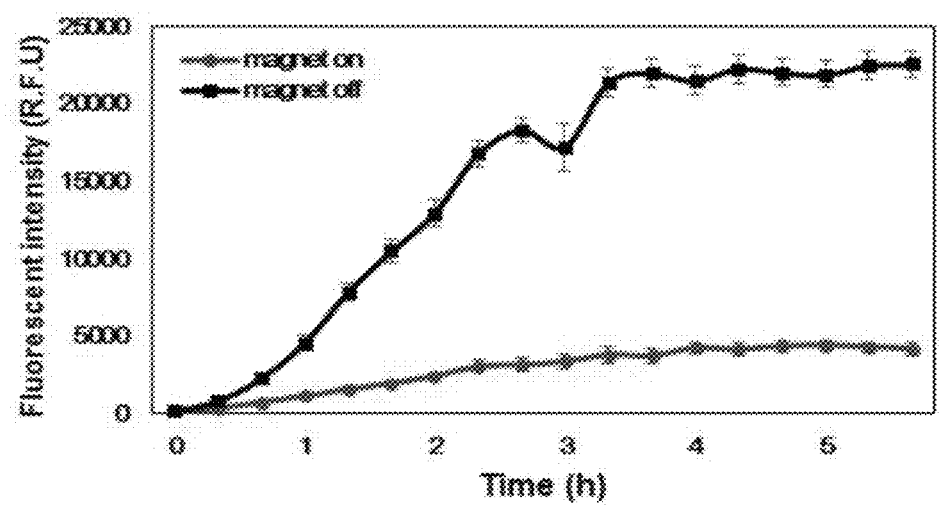
FIG. 11D illustrates the results of the regulatory experiment of the gene expression by applying a magnetic field.

The graph of the control group ("magnet off" and black graph) of FIG. 11D follows the usual pattern of protein expression. On the other hand, it was confirmed that the graph of the experimental group ("magnet on" and red graph), which has undergone the expression inhibitory mechanism provided in the present disclosure, shows a low level of the expression over the overall culture time. Thus, it was confirmed that the expression inhibitory mechanism of the present disclosure works from the beginning of the expression to finally induce a difference in the expression to the extent as illustrated in FIG. 13

Example 13. Comparison of Regulation Level of GFP DNA Expression with Time of Magnetic Field Application GFP DNA attached to the polymer-iron oxide composite was incubated in an incubator at 30° C. in the same manner as described in Example 11. A neodymium magnet was placed at the bottom of the tube after 0, 0.5, 2, and 6 hours, respectively, after incubation. After 8 hours of incubation, the mixture was centrifuged at 10,000 g for 10 minutes at 4° C. 10 µl of the supernatant was extracted and diluted 10 times, and each fluorescence values of GFP was measured and compared using a spectroscopic analyzer. The comparison results are illustrated in FIGS. 14A and 14B.

Figure 14A:
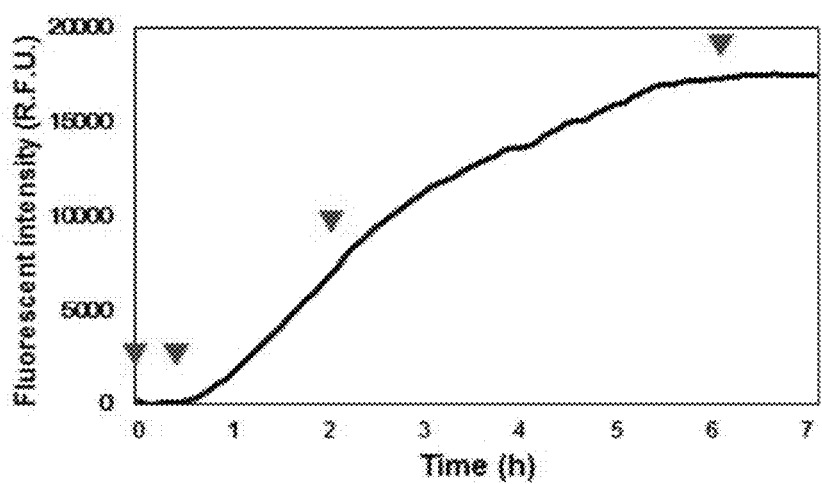
FIG. 14A is a view illustrating the degree of gene expression when a magnetic field is not applied to DNA-containing polymer-iron oxide composite nanostructure prepared according to an embodiment of the present disclosure.

FIG. 14A illustrates the change in fluorescence value caused by GFP expression obtained by incubating for 7 hours in the absence of a magnet. The magnet was positioned at the time indicated by the inverted triangle in the graph. FIG. 14B is a graph illustrating the relative fluorescence values of GFP obtained finally when the magnet was positioned at each time point.

Figure 14B:
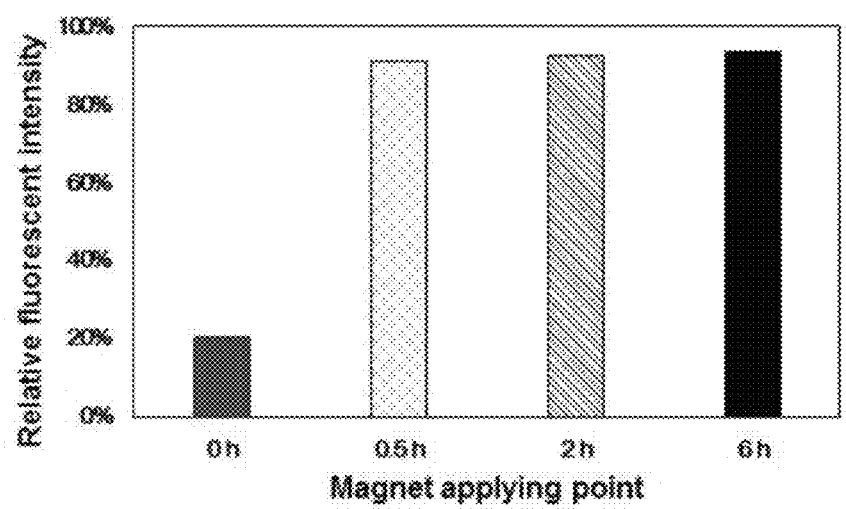
FIG. 14B is a view illustrating the degree of gene expression when a magnetic field is applied to DNA-containing polymer-iron oxide composite nanostructure prepared according to an embodiment of the present disclosure.

As illustrated in FIG. 14B, activation of the expression inhibitory mechanism after 30 minutes from the start of expression did not affect the amount of GFP expressed finally. In other words, this means that when the transcription process is not inhibited at the initial stage, although the mechanism is activated after 30 minutes therefrom, the protein translation process is carried out by the previously transcribed mRNA so that the expression level thereof is finally the same as that of the control group. Therefore, when the mechanism as described above is activated at the same time as the start of expression, the final amounts of expression are different, which means that the mechanism as suggested in the present disclosure inhibits transcription of mRNA.

It should be understood that the foregoing description of the present disclosure is for illustrative purposes only and that those of ordinary skill in the art to which the present disclosure pertains are capable of easily transforming to other specific forms without altering the technical concept or essential features of the present disclosure. Therefore, it should be understood that examples are illustrative in all aspects and not restrictive.

From the foregoing, it will be appreciated that various embodiments of the present disclosure have been described herein for purposes of illustration and that various modifications may be made without departing from the scope and spirit of the present disclosure. Accordingly, the various embodiments disclosed herein are not intended to be limiting, with the true scope and spirit being indicated by the following claims.

What is claimed is:

1. A method of reducing expression of a gene, the method comprising:
    incubating a polymer-iron oxide composite nanostructure comprising a DNA encoding the gene in an incubator comprising a DNA expression kit for the DNA at 30° C. for 8 hours, while applying a magnetic field to the polymer-iron oxide composite nanostructure by a neodymium magnet placed at a bottom of the incubator; and
    confirming the reduction in gene expression when the polymer-iron oxide nanostructure is incubated in the presence of the magnetic field,
    wherein the polymer-iron oxide composite nanostructure comprises;
    a polymer-iron oxide composite nanoparticle;
    a silica coating layer coated on a surface of the polymer-iron oxide composite nanoparticle; and
    the DNA encoding the gene and attached to the silica coating layer.

* * * * *